United States Patent [19]

Bernstein et al.

[11] Patent Number: 4,499,299
[45] Date of Patent: Feb. 12, 1985

[54] PHARMACEUTICALLY ACTIVE PHENYLCARBOXYLIC ACID DERIVATIVES

[75] Inventors: Peter R. Bernstein; Alvin K. Willard, both of Wilmington, Del.

[73] Assignee: ICI Americas Inc., Wilmington, Del.

[21] Appl. No.: 447,467

[22] Filed: Dec. 6, 1982

[30] Foreign Application Priority Data

Dec. 30, 1981 [GB] United Kingdom ................. 8139027

[51] Int. Cl.$^3$ ............................................. C07C 65/40
[52] U.S. Cl. ................................... 514/570; 562/434; 562/438; 562/464; 560/21; 560/53
[58] Field of Search ....................... 562/464, 434, 438; 560/21, 53

[56] References Cited

FOREIGN PATENT DOCUMENTS 0028063 5/1981 European Pat. Off. .
2058785 4/1981 United Kingdom .

Primary Examiner—Paul J. Killos
Attorney, Agent, or Firm—John M. Sheehan; David J. Levy

[57] ABSTRACT

Compounds which antagonize the slow-reacting substance of anaphylaxis or components thereof, e.g., leukotrienes, in warm blooded animals as well as intermediates and methods for their preparation, pharmaceutical compositions and methods for their administration. The compounds are diphenyl carboxylic acids with particular linking groups between the individual phenyl rings and the carboxylic acid moiety. Particular utilities are to relieve asthma and inflammation in man.

14 Claims, No Drawings

PHARMACEUTICALLY ACTIVE PHENYLCARBOXYLIC ACID DERIVATIVES

The present invention relates to compounds which antagonize the slow-reacting substance of anaphylaxis (hereinafter "SRS-A") or components thereof and thus relieve pulmonary problems such as bronchial asthma in humans. The role of SRS-A in allergy and inflammation is described in Science, Vol. 215 Mar. 12, 1982, pages 1380–1383.

Compounds having some structural similarity to those of the present invention are described by R. A. Appelton et al in the Journal of Medicinal Chemistry, Vol. 20, No. 3, pages 371–379 (1977).

SUMMARY OF THE INVENTION

The present invention comprises compounds which are SRS-A antagonists and are useful in the treatment of conditions such as hay fever and obstructive airways diseases, e.g., asthma, bronchitis and bronchorrhea. The invention compounds are hydroxyacetophenones having a phenyl ring attached through a chain and a carboxylic acid moiety attached directly or indirectly to the phenyl ring as described below. Also part of the present invention are pharmaceutical compositions containing one or more of the compounds and their use, methods for the preparation of the compounds and intermediates used in the syntheses.

DETAILED DESCRIPTION OF THE INVENTION

Compounds of the present invention are of the following formulae (I), (II) or (III):

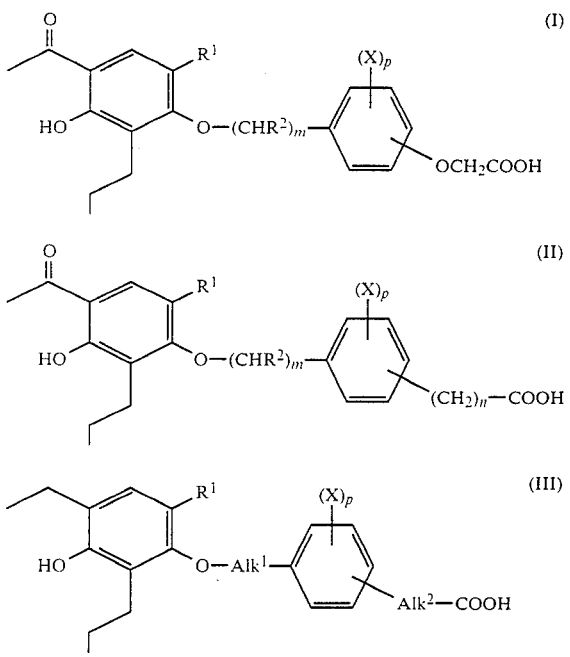

wherein
$R^1$ is hydrogen or iodine;
$R^2$ is hydrogen, lower alkyl, phenyl or phenyl substituted with one to three halogen, alkyl or alkoxy groups;
X is independently halogen, nitro, hydroxy, lower alkyl or lower alkoxy;

$Alk^1$ and $Alk^2$ are independently a direct bond; lower alkenyl; lower alkenyl substituted by lower alkyl, halogen, phenyl or phenyl substituted with one to three halogen, alkyl or alkoxy groups; lower alkylene; or lower alkylene substituted by lower alkyl, halogen, phenyl or phenyl substituted with one to three halogen, alkyl or alkoxy groups; wherein at least one of $Alk^1$ and $Alk^2$ is lower alkenyl or substituted lower alkenyl;

m is 0, 1, 2 or 3 with the proviso that if m is 2 or 3, $R^2$ is hydrogen;
n is 0, 1, 2 or 3; and
p is 0, 1 or 2 and the pharmaceutically acceptable base-addition salts thereof.

As used in this specification, "lower alkyl" is alkyl of about 1 to 6 carbons, "lower alkoxy" is alkoxy of about 1 to 6 carbons, "lower alkenyl" is alkenyl of about 2 to 6 carbons and "lower alkylene" is alkylene, also known as methylene or polymethylene, of about 1 to 6 carbons. It is to be understood that compounds of the invention can exist in various isomeric forms and the invention embraces all of these, e.g, the isomers which result from asymmetry at —$CHR^2$— when $R^2$ is other than hydrogen, the various isomers formed by the placement of the X and —$OCH_2COOH$ and —$(CH_2)_m$—COOH groups on the benzene ring and the cis and trans isomers resulting from $Alk^1$ and/or $Alk^2$ being alkenyl or substituted alkenyl.

A suitable base-addition salt of the phenyl compound of the invention is, for example, a salt formed with alkali metal hydroxides or carbonates such as sodium hydroxide or potassium carbonate or with ammonia or a primary, secondary or tertiary amine such as ethylamine, dimethylamine or triethanolamine.

A particular value for $R^1$ is hydrogen.

A particular value for $R^2$ when it is lower alkyl is methyl, ethyl, propyl or butyl, A particular value for the substitution on the phenyl group is a halogen group such as a fluoro, chloro, bromo or iodo group, a lower alkyl group such as a methyl, ethyl, propyl or butyl group, lower alkoxy group such as a methoxy, ethoxy, propoxy or butoxy group or any combination of these groups.

A particular value for X is one or more, same or different, fluoro, chloro, bromo or iodo groups, methyl, ethyl, propyl or butyl groups or methoxy, ethoxy, propoxy or butoxy groups.

A particular value for $Alk^1$ and/or $Alk^2$ is alkenyl or substituted alkenyl of 2 or 3 carbons in the alkenyl chain, such as propenyl, e.g., in formula (III) reading from left to right, $Alk^2$ is ethenyl, methyleneethenyl (—$CH_2$—CH=CH—) or ethenylmethylene (—CH=CH—$CH_2$—). Preferably, only one of $Alk^1$ and $Alk^2$ is alkenyl or substituted alkenyl, in particular $Alk^2$. If $Alk^1$ is alkenyl or substituted alkenyl, the double bond is preferably at least one carbon removed from the oxygen attached to the acetophenone ring. Another particular value for $Alk^1$ or $Alk^2$ is alkylene or substituted alkylene of 1, 2 or 3 carbons in the alkylene chain, e.g., methylene. Particular values for the alkyl substitution on the alkenyl or alkylene groups or on the phenyl group which is itself substituted on the alkenyl or alkylene group are lower alkyls such as methyl, ethyl, propyl or butyl. Particular values for the halogen substitution on the alkenyl or alkylene groups or on the phenyl group which is itself substituted on the alkenyl or alkylene group are independently fluoro, chloro, bromo or iodo. Particular values for the alkoxy substitution on the phenyl group which is substituted on the alkyl or alkylene group are lower alkoxy groups such as methoxy, ethoxy, propoxy or butoxy groups.

A particular value for m is 0 or 1; for n is 0 or 1; and for p is 0 or 1.

Particular groups of compounds of the formula (I) are the following:

1. $R^1$ is hydrogen; $R^2$ is hydrogen; m is 1; p is 0; and the —OCH$_2$COOH group is meta or para.

2. $R^1$ is hydrogen; m is 0; p is 0; and the —OCH$_2$COOH group is ortho, meta or para.

Particular groups of compounds of the formula (II) are the following:

3. $R^1$ is hydrogen; $R^2$ is hydrogen; m is 1; n is 0; and the —COOH group is para to the —CHR$^2$— group.

4. $R^1$ is hydrogen; $R^2$ is methyl or phenyl; m is 1; p is 0; n is 0; and the —COOH group is para to the —CHR$^2$— group.

5. $R^1$ is hydrogen; $R^2$ is hydrogen; m is 1; p is 0; n is 1; and the —CH$_2$COOH group is meta or para to the —CHR$^2$— group.

6. $R^1$ is hydrogen; m is 0; p is 0; n is 0; and the —COOH group is ortho, meta or para to the —O— group.

7. $R^1$ is hydrogen; m is 0; p is 0; n is 1; and the —CH$_2$COOH group is ortho, meta or para to the —O— group.

8. $R^1$ is hydrogen; $R^2$ is hydrogen; m is 1; n is 0; p is 1; X is lower alkoxy and is ortho to the —CHR$^2$— group; and the —COOH group is para to the —CHR$^2$— group.

9. $R^1$ is hydrogen; $R^2$ is hydrogen; m is 1; n is 0; p is 1; X is halogen and is meta to the —CHR$^2$— group; and the —COOH group is para to the —CHR$^2$— group.

Particular groups of compounds of the formula (III) are the following:

10. $R^1$ is hydrogen; Alk$^1$ is methylene; p is 0; Alk$^2$ is trans ethenyl and is meta or para to Alk$^1$.

11. $R^1$ is hydrogen; Alk$^1$ is methylene; p is 1; X is lower alkoxy and is ortho to Alk$^1$; Alk$^2$ is trans ethenyl and is meta or para to Alk$^1$.

Compounds of formula (I), (II) and (III) may be prepared by (a) condensing compounds of the formulae (IV) and (V) or (IV) and (VII) to yield an ester of formula (VI) or (VIII), respectively, followed by saponification, if $R^4$ is other than hydrogen, according to the following synthetic scheme:

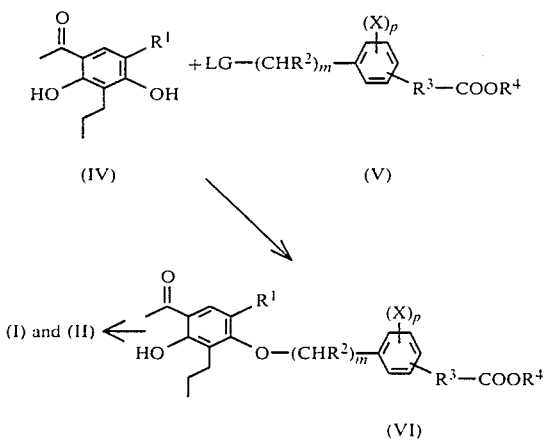

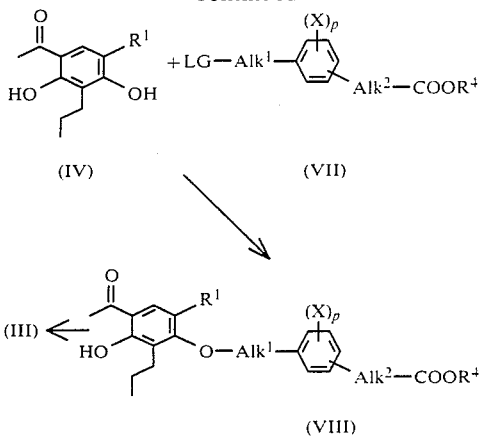

wherein LG is a leaving group displaceable by a phenolic hydroxy, e.g., a halogen such as bromo, a sulfonate ester, e.g. p-toluene-sulfonate; $R^3$ is either —OCH$_2$— or —(CH$_2$)$_n$— for compound (I) or (II), respectively; $R^4$ is hydrogen or an organic moiety which is easily replaceable by hydrogen without change to the remainder of the molecule, e.g., a saturated or unsaturated alkyl or aryl group such as a lower alkyl group; and $R^1$, $R^2$, X, Alk$^1$, Alk$^2$, m, n and p are as defined for formulae (I), (II) and (III).

Compounds of formula (IV) are known as seen by a reading of U.S. Pat. No. 4,252,818 and R. A. Appleton et al. in J. Med. Chem., 1977, 20, pages 371-379.

Compounds of formula (V) are prepared by placement of the LG group on a compound of the following formula (IX):

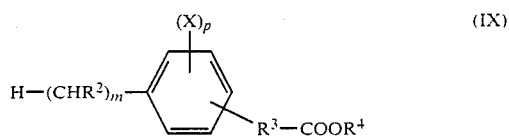

wherein $R^2$, $R^3$, $R^4$, X, m, n and p are as defined for formula (V), e.g., by bromination with bromine or N-bromosuccinimide when m=1. The LG group can be introduced by conversion of the corresponding alcohol (the alcohol being provided, for example, by reduction of the corresponding ketone or aldehyde with an agent such as sodium cyanoborohydride or sodium borohydride) to a sulfonate ester, such as, for example, the methane sulfonate or the p-toluenesulfonate esters, or by conversion of the alcohol to a halogen such as by treatment with phosphorous tribromide or with thionyl chloride. Alternatively, when m=0, LG can be fluoro or a trifluoromethyl-sulfonate ester of an appropriately substituted phenol. The ester of formula (IX) may be prepared from the corresponding carboxylic acid by treatment with an alcohol of the formula R$^4$OH either by pretreating with a reagent to halogenate the carboxylic acid to produce the intermediate acid halide or simply in the presence of a mineral acid such as HCl. Alternatively, the esters may be prepared by treatment of a salt of the carboxylic acid, such as the potassium salt with alkyl halides such as methyl iodide or ethylbromide in a polar aprotic solvent such as N,N-dimethylformamide or dimethylsulfoxide.

Compounds of formula (VII) are prepared by placement of the LG group on a compound of the following formula (X):

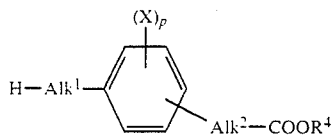

wherein $Alk^1$, $Alk^2$, X, p and $R^4$ are as defined for formula (VII), e.g., by bromination with bromine or N-bromosuccinimide. The LG group can be introduced by conversion of the corresponding alcohol, the alcohol being provided, for example, by reduction of the corresponding ketone or aldehyde with an agent such as sodium cyanoborohydride or sodium borohydride, to a sulfonate ester, such as, for example, the methane sulfonate or the p-toluenesulfonate esters, or by conversion of the alcohol to a halogen such as by treatment with phosphorous tribromide or with thionyl chloride. Alternatively, when $Alk^1$ is a direct bond, LG can be fluoro or a trifluoro-methylsulfonate ester of an appropriately substituted phenol. The ester of formula (X) may be prepared from the corresponding carboxylic acid by treatment with an alcohol of the formula $R^4OH$ either in the presence of a reagent to halogenate the carboxylic acid to produce the intermediate acid halide or simply in the presence of a mineral acid such as HCl. Alternatively, the esters may be prepared by treatment of a salt of the carboxylic acid, such as the potassium salt with alkyl halides such as methyl iodide or ethylbromide in a polar aprotic solvent such as N,N-dimethylformamide or dimethylsulfoxide. The double bond of the alkenyl of $Alk^1$ or $Alk^2$ may be placed by a Wittig reaction. For example, if $Alk^1$ is ethenyl and $Alk^2$ is a direct bond in formula (VII), the compound may be prepared by reacting an ester-substituted benzaldehyde such as CHO-Phenyl-$COOR^4$ with a Wittig reagent such as formylmethylene triphenylphosphorane to yield the corresponding cinnamaldehyde which may be reduced to the alcohol with a reducing agent such as sodium borohydride and brominated to the bromide with a brominating agent to yield the compound of formula (VII) wherein LG is bromo, $Alk^1$ is ethenyl and $Alk^2$ is a direct bond.

The condensation reaction between compounds of formula (IV) and (V) and (IV) and (VII) can take place in solvents such as acetone or butanone at temperatures of about 25° to 100° C. In some cases, it is beneficial to have sodium or potassium iodide present in the reaction mixture. The saponification of compounds of formula (VI) or (VIII) to yield formula (I) or (II) or (III), respectively, can take place in solvents such as water, tetrahydrofuran, ethanol or methanol at temperatures of about 25° C. to the reflux temperature of the solvent with saponification agents such as lithium hydroxide or potassium carbonate.

Alternatively, compounds of formulae (I) and (II) may be made by the following processes, wherein $R^1$, $R^2$, $R^3$, $R^4$, X, m, n and p are as defined above unless otherwise indicated:

(b) dealkylating a compound of the following formula (XI):

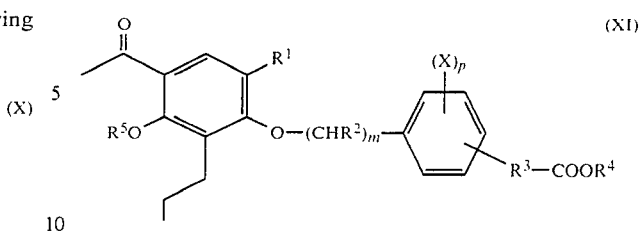

wherein $R^5$ is alkyl, e.g. lower alkyl of 1 to 6 carbons, by treatment with a mercaptide anion, e.g. $LiSCH_3$ or $NaSCH_2CH_2CH_3$ under anhydrous conditions. The analogous technique can be used to prepare compounds of formula (III) from the corresponding ethers;

(c) hydrolyzing a compound of the following formula (XII) by treatment with acid or base, e.g. aqueous sodium hydroxide or aqueous HCl:

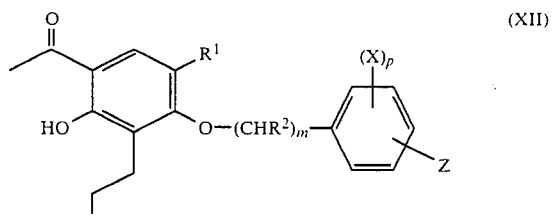

wherein Z is $-R^3-CN$; $-R^3CONR^6R^6$; $-R^3C(NR^6)OR^6$ and other derivatives with the same oxidation state as the desired carboxylic acid, wherein $R^6$ is hydrogen or alkyl, e.g. lower alkyl of 1 to 6 carbons which may be linked to another $R^6$ in the group such as piperidinyl and $R^3$ is as defined above for formula (V). Compounds of formula (III) may be prepared by the analogous reaction on compounds of formula (XII) wherein $-(CHR^2)_m-$ and $R^3$ are replaced by $Alk^1$ and $Alk^2$, respectively, as defined for formula (III);

(d) iodination of compounds of formula (XI), or the analogous compounds of the formula (III) series, wherein $R^1$ and $R^5$ are hydrogen, with, for example $KI_3$ in the presence of a base such as aqueous ammonium hydroxide;

(e) oxidation of compounds of the formula (XII), or the analogous compounds of the formula (III) series, wherein $R^1$ is hydrogen and Z is $-R^3CH_2OH$ with, for example, a chromium compound such as $CrO_3$ in acidic aqueous acetone, also known as a Jones oxidation, $R^3$ being as defined above for formula (V);

(f) alkylation of compounds of formula (XII), or the analogous compounds of the formula (III) series, wherein Z is $-OH$, with compounds of the formula $LG-CH_2COOR^7$, wherein LG is as defined above for formula (V) and $R^7$ is alkyl such as lower alkyl of 1 to 6 carbons, the alkylation taking place in a solvent such as acetone or butanone in the presence of potassium carbonate; and (g) carefully hydrogenating compounds of formula (XII) wherein Z is $-R^3COOH$ and there is a double bond at the terminal carbons of the n-propyl chain of the acetophenone ring, i.e. the $-CH_2CH_2CH_3$ group is a $-CH_2-CH=CH_2$ group, and $R^3$ is as defined above for formula (V), the hydrogenation taking place in the presence of a catalyst such palladium on carbon in a solvent such as ethanol or methanol.

The pharmaceutically-acceptable salts may be prepared by contacting the acidic and basic entities, usually in a stoichiometric ratio, in either an aqueous, non-aqueous or partially aqueous medium, as appropriate. The salts are recovered either by filtration, by precipitation followed by filtration, by evaporation of the solvent, as appropriate, or, in the case of aqueous solution, by lyophilization. Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine; secondary amines, such as diethyl-amine, morpholine, pyrrolidine and piperidine; tertiary amines, such as triethylamine, triethanolamine, N-ethylpiperidine, N-methylmorpholine and aromatic amines such as pyridine; hydroxides, such as sodium hydroxide; alkoxides, such as sodium methoxide and potassium methoxide; hydrides, such as calcium hydride and sodium hydride; and carbonates, such as potassium carbonate and sodium carbonate.

Also part of the present invention are novel intermediates and processes used to prepare compounds of the formula (I), (II) and/or (III). In particular, compounds of the formulae (V), (VI), (VII), (VIII) and (IX), e.g. where $R^4$ is lower alkyl of 1 to 6 carbons, and compounds of the formula (XII) described above in process (c) wherein Z is $-R^3-CN$; $-R^3CONR^6R^6$; and $R^3C(NR^6)OR^6$ wherein $R^6$ is hydrogen or alkyl, e.g. lower alkyl of 1 to 6 carbons, which may be linked to another $R^6$ in the group such as piperidinyl and $R^3$ is as defined above for formula (V) are useful intermediates. Compounds of formulae (VI) and (VIII) are valuable intermediates and/or would be useful as SRS-A antagonists as the compounds of formulae (I), (II) and (III).

Compounds of the formulae (I), (II) and (III) are antagonists of SRS-A and may be used in disease states where it is desirable to antagonize the effects of SRS-A or components thereof. In particular, compounds of formulae (I), (II) and (III) will antagonize one or more of the arachidonic acid metabolites known as leukotrienes $B_4$, $C_4$ and $D_4$, or reduce the effective production of one or more of these metabolites, e.g. by inhibiting the biosynthesis of one or more of these metabolites, for example by inhibiting at least in part, the enzyme 5'-lipoxygenase as explained by R. A. Lewis in Nature, Vol. 293, pages 103-108 (1981) and by E. J. Goetzl in The New England Journal of Medicine, Vol. 303, pages 822-825 (1980). The leukotrienes $B_4$, $C_4$ and $D_4$ are known to be powerful spasmogens, particularly in the lung, and are known to increase vascular permeability and are implicated in allergy and inflammation. The compounds of formulae (I), (II) and (III) are useful in the treatment of inflammation, impaired vascular permeability and/or spasm in warm blooded animals including man, e.g., in the treatment of pulmonary diseases such as reversible obstructive airways diseases, e.g., asthma or other allergic diseases such as hay fever, bronchospastic attack or allergic rhinitis, in the treatment of arthritis or in the treatment of cardiovascular diseases. Also part of the invention are pharmaceutical compositions suitable for administration to humans comprising a compound of formula (I), (II) or (III) or a pharmaceutically acceptable salt thereof and a pharmaceutically acceptable carrier or diluent. The composition may be administered orally or parenterally, e.g., by intravenous, intramuscular, intraperitoneal, subcutaneous or topical administration or by inhalation, in the form of, for example, tablets, capsules, aqueous or oily solutions or suspensions, emulsions, dispersible powders, suppositories, sterile injectable aqueous or oily solutions or suspensions, gels, creams, ointments or lotions. For oral administration, a tablet or capsule may be used containing between 5 mg and 250 mg of a compound of formula (I), (II) or (III). A sterile injectable solution or suspension may contain between 0.1% and 10% w/w of the compound of formula (I), (II) or (III) while a topical formulation would contain 1.0 to 10% w/w.

The dosage of a compound of formula (I), (II) or (III) will depend on the particular symptoms of the patient as well as the patient's age, weight, and previous response. An effective dosage would generally be in the range of about 1 to 5 mg per kilogram of body weight. In general the dosage for an average human will range from about 50 mg to 1000 mg per day, preferably about 20 mg to 500 mg in a single or multiple administration.

Activity of the compounds of the invention as slow-reacting substance of anaphylaxis antagonists may be demonstrated on standard tests, for example by the ability of the compound of formula (I), (II) or (III) to antagonize and inhibit contractions of an isolated guinea pig trachea as induced by leukotriene $C_4$ or $D_4$ as follows.

Male Hartley guinea pigs weighing 300-500 g are killed and exsanguinated. The trachea is immediately resected, cleaned of adhering connective tissue and cut into a spiral strip measuring approximately 3 to 5 mm $\times 20$ to 25 mm. The strip is mounted in a 10 ml jacketed tissue bath by tying one end to a tissue hook and the opposite end to a Grass FT03C force-displacement transducer connected to an 8-channel Beckman Polygraph for recording contractile or relaxant responses. The tissue is bathed in modified Krebs' solution (37.5° C.) of the following composition (mM): NaCl, 119; KCl, 4.6; $CaCl_2$, 1.8; $MgCl_2$, 0.5; $NaHCO_3$, 24.9; $NaH_2PO_4$, 1.0; glucose, 11.1. Indomethacin, a cyclooxygenase inhibitor, is also present in a concentration of $5 \times 10^{-6}$M. The tissue baths are constantly aerated with 95% $O_2$ and 5% $CO_2$. Tissues are placed under a passive tension of 2 g and allowed a 50 minute equilibration period before beginning experiments. This technique is standard for studying the effects of drugs on airway smooth muscle (Krell, R. D., J. Pharmacol. Exp. Ther. 211: 436, 1979; Kneussel, M. P. and Richardson, J. B., J. Appl. Physiol. 45: 307, 1978; Fleisch, J. H. and Calkins, P. J., J. Appl. Physiol. 41: 62, 1976).

Tissues are set up in groups of eight—four are used as time/vehicle controls and the remaining four for experimental compounds. No fewer than 4 tissues are used for each test compound. All tissues are exposed to $8 \times 10^{-9}$M $LTD_4$, following the 50 minute equilibration period, and the response recorded. This concentration of $LTD_4$ is that which produces a contraction equal to about 70-80% of the maximal effect of the agonist in this tissue. The $LTD_4$ is washed out for 20-25 minutes and the procedure repeated twice to insure that reproducible responses are being obtained with $LTD_4$. $LTC_4$, at a concentration of $8 \times 10^{-9}$M, may be substituted for $LTD_4$ in the same procedure.

Once tissue reproducibility has been established test compounds are added to four baths following the 20 to 35 minute washout period. After a 10 minute incubation with test compound or vehicle $8 \times 10^{-9}$M LT's are added and the response recorded. Percent inhibition by the test compound or percent change in vehicle controls is calculated, for each tissue, according to the following equation: % inhibition = 100 multiplied by (mg tension increase of preceding response minus mg tension increase in presence of compound) divided by mg tension increase of preceding response. The means of the percent changes for vehicle controls and test compound are calculated and evaluated for significant differences by Students' t-test for unpaired data. Tissues exposed to agents were retested for responsiveness to LTD$_4$ or C$_4$ following a 25 minute washout period. If tissue responsiveness was equal to responsiveness preceding exposure to the test compound additional studies were conducted. If responsiveness is not restored by the washing procedure, the tissues are discarded.

In general, activity as an SRS-A antagonist is demonstrated in the above-described test by significant inhibition at about $10^{-4}$ molar, e.g., an IC$_{50}$ of about $10^{-4}$ molar or less. Particularly active compounds of the invention are those of Example 7 for formula (I), of Example 4 for formula (II) and Examples 16 and 22 for formula (III).

For compounds which produced a significant inhibition of LTC$_4$- or D$_4$-induced contraction further studies were conducted in separate tissues, with a nonspecific spasmogen viz., BaCl$_2$, to insure that the inhibition obtained was specific for the leukotrienes and not related to a nonspecific depression of the smooth muscle. Basically, the procedure was the same as described above for LTC$_4$ and D$_4$ except that $3 \times 10^{-3}$M BaCl$_2$ was used as the spasmogenic agent. Indomethacin, $5 \times 10^{-6}$M, is present for all experiments. A maximal response of the tissues to histamine ($10^{-4}$M) was determined following a 50 minute equilibration period. After histamine was washed out for 60 minutes, test compound was added to four tissues. After 10 minutes incubation with test compound and vehicle, $3 \times 10^{-3}$M BaCl$_2$ was added and the response, expressed as percentage of histamine maximal response, recorded. Significant differences between responses for control and test compound treated tissues were evaluated by unpaired Students t-test. Percent inhibition by compound was calculated according to the following equation: % inhibition = 100 multiplied by (mean response of control tissues minus mean response of test compound treated tissues) divided by mean response of control tissues.

The reduction of the effective production of leukotrienes may be measured and evaluated by the following test which is a modification of the procedure reported by M. K. Bach in The Journal of Immunology, Vol. 113, No. 6, pages 2040-2044 (1974). Preparation of Rat Peritoneal Cells—Male Sprague Dawley rats weighing 200-300 g were used. Rate peritoneal cells (RPC) were obtained as peritoneal washings using Tyrodes buffer (pH 6.8) containing 1 unit of heparin per ml. The cells were washed twice in heparin-free Tyrodes and resuspended in challenge medium (pH 6.8) containing 1% w/v gelatin and (mM): NaCl, 140; KCl, 2.6; CaCl$_2$ 1.1; NaHCO$_3$, 11.9, NaH$_2$PO$_4$, 0.4; N-2-hydroxyethyl piperazine-N-2 ethane sulfonic acid (HEPES), 5.0; 2(N-morpholino)ethane sulfonic acid (MES) 5.0; and glucose, 5.5. The composition of this cell preparation was: $64.7 \pm 1.2\%$ macrophages, $14.6 \pm 1.8\%$ eosinophils, $17.7 \pm 1.7\%$ lymphocytes, $3.1 \pm 0.4\%$ neutrophils and $2.3 \pm 0.3\%$ mast cells (mean $\pm$ standard error (SE) of 3 cell batches prepared from 3 rats each). Protein was analyzed by the method of M. Bradford in Analytical Chemistry, Vol 72, pages 248-254 (1976) and found to be $77 \pm 3$ micrograms per $10^6$ RPC (mean $\pm$ SE of triplicate determinations in 3 experiments). Cell viability was determined by trypan blue exclusion and was consistently greater than 90%. Incorporation of [$^3$H] into Rat Peritoneal Cells—Peritoneal cells were labeled in bulk with [$^3$H]-aracadonic acid (78-92 curies per millimole, 2 microcuries per $2.5 \times 10^6$ cells/ml) in 50 ml plastic conical tubes for 30 minutes at 30° C. The cells were then centrifuged and resuspended in challenge medium ($4$–$5 \times 10^6$ cells per ml). Aliquots (0.9 ml) of the labeled suspension were preincubated with test compounds for 10 minutes at 30° C. and then challenged with various concentrations of A23187, as defined by M. Bach, Journal of Immunology, Vol. 113, No. 6, pages 2040-2044 (1974), for 20 minutes. Separation and Identification of [$^3$H]-Arachidonate Metabolites—The following method was employed in order to isolate, separate and identify the [$^3$H] leukotrienes generated in RPC in response to A23187 in the presence or absence of test compounds; the cells were pelleted by centrifugation and the resulting supernatant (1 ml) was added to 4 ml of ethanol which contained carrier leukotrienes (3 nanomoles of LTC$_4$, LTD$_4$, LTE$_4$) and stored overnight at $-20°$ C. The precipitated protein was removed by centrifugation ($2000 \times$ gravity, 20 minutes, $-10°$ C.) and a small aliquot (50 microliters) of the supernatant was counted to monitor total [$^3$H]-metabolite release. The remaining supernatant was evaporated under N$_2$ to dryness, resuspended in methanol (100 microliters) and applied to a silicic acid column (Silicar CC-7, Mallinkrodt, 10 cm$\times$0.4 cm) pre-equilibrated with ethyl acetate. The columns were washed with 6 ml of ethyl acetate:methanol 90:10, (v/v) to remove less polar metabolites (i.e. prostaglandins and hydroxy acids). [$^3$H] leukotrienes were eluted with 4 ml of methanol. The methanol fraction was evaporated to dryness and resuspended in a high pressure liquid chromatography solvent of methanol:water:acetic acid, 68:32:0.1 v/v/v, pH 5.8. The samples were subjected to reverse phase high pressure liquid chromatography (5 micron Ultrasphere ODS column, Beckman Instruments Model 110A pump) and eluted isocratically at 1.5 ml per minute. Fractions absorbing at an optical density of 280 nanometers on a Beckman Analytical Optical Unit corresponding to the various LT standards were collected for liquid scintillation counting. The absorbance of the various LTs was plotted and calculated as area under the curve, by a Hewlett-Packard integrator (Model 3390A). Fractions (0.5 ml) were counted in a Beckman liquid scintillation spectrometer (LS7500). Unless indicated otherwise corrections for recovery of carrier LT were routinely made. This test effectively monitored the inhibition of LT synthesis as described above.

In the following examples and throughout the specification, the following abbreviations are used: mg (milligrams); g (grams); mm (millimeters); ml (milliliters); mM (millimolar); M (molar); N (normal); bp (boiling point); mp (melting point); °C. (degrees Centigrade); LT (leukotriene); NMR (nuclear magnetic resonance); THF (tetrahydrofuran); MeOH (methanol); mmoles (millimoles); TLC (thin layer chromatography); and the conventional symbols for the chemical elements.

EXAMPLE 1

4-(4-Acetyl-3-hydroxy-2-propylphenoxy)methylbenzoic acid a. Methyl 4-methylbenzoate

To 200 ml of methanol at 0° was added, with stirring, 48.4 g (0.312 mole) of 4-methylbenzoyl chloride over 20 minutes. Following the addition, the reaction mixture was stirred at room temperature for one hour. The methanol was evaporated and the residue was distilled to give 43 g of the title compound as a colorless liquid: boiling point 103°–108° C. at 20 mm of Hg.

b. Methyl 4-bromomethylbenzoate

A solution of 15.0 g (0.1 mole) of methyl 4-methylbenzoate in 150 ml of carbon tetrachloride was stirred and heated to reflux with a 350 watt tungsten lamp. A solution of 16.0 g (0.1 mole) of bromine in 150 ml of carbon tetrachloride was added over 3 minutes by an addition funnel. The colorless reaction mixture was evaporated to give 22.03 g (97% yield) of the title compound as colorless prisms.

c. Methyl 4-(4-acetyl-3-hydroxy-2-propylphenoxy)methylbenzoate

A solution of 1.0 g (5.15 mmoles) of 2,4-dihydroxy-3-propylacetophenone, see R. A. Appleton et al. in J. Med. Chem. 1977, 20, pages 371–379, and 1.77 g (7.7 mmoles) of methyl 4-bromomethylbenzoate in 20 ml of acetone was treated with 784 mg (5.66 mmoles) of $K_2CO_3$ and stirred at reflux for 15 hours. The reaction mixture was diluted with ether, washed with water and saturated aqueous $NaHCO_3$ solution and dried with $MgSO_4$. Evaporation of the solvent gave an oil which crystallized. This material was purified by chromatography on silica gel with 30% hexane/dichloromethane as eluent to provide 1.212 g (69% yield) of the title compound as a white powder mp 99.5°–100.5° C.

d. 4-(4-acetyl-3-hydroxy-2-propylphenoxy)methylbenzoic acid

A solution of 684 mg (2.0 mmoles) of methyl 4-(4-acetyl-3-hydroxy-2-propylphenoxy)methylbenzoate in 9 ml MeOH, 9 ml tetrahydrofuran and 3 ml water was treated with 420 mg (10 mmoles) $LiOH.H_2O$ and stirred at room temperature for 4 hours. The reaction mixture was diluted with water, acidified by addition of concentrated HCl and extracted with dichloromethane. The combined extracts were washed with water, dried with $MgSO_4$ and evaporated to give a white solid. Recrystallization of this material from ether gave 416 mg (63% yield) of the title compound as fine white needles mp 188°–188.5° C.

Analysis: Calculated for $C_{19}H_{20}O_5$: C, 69.50; H, 6.14. Found: C, 69.17; H, 6.41.

EXAMPLE 2

2-(4-Acetyl-3-hydroxy-2-propylphenoxy)methylbenzoic acid

The title compound was prepared by methods analogous to those in Example 1, sections a., b., c. and d. with the melting point of methyl 2-(4-acetyl-3-hydroxy-2-propylphenoxy)methylbenzoate being 78°–81° C. Recrystallization of the title compound from ether gave a solid, mp 214°–216° C.

Analysis: Calculated for $C_{19}H_{20}O_5$: C, 69.50; H, 6.14. Found: C, 69.44; H, 6.18.

EXAMPLE 3

3-(4-Acetyl-3-hydroxy-2-propylphenoxy)methylbenzoic acid

The above-named compound was prepared by methods analogous to those in Example 1, sections a., b., c. and d with the melting point of methyl 3-(4-acetyl-3-hydroxy-2-propylphenoxy)methylbenzoate being 139.5°–140.5° C. Recrystallization of the title compound from ether gave a solid, mp 216°–220° C.

Analysis: Calculated for $C_{19}H_{20}O_5$: C, 69.50; H, 6.14. Found: C, 69.11; H, 6.32.

EXAMPLE 4

3-Methoxy-4-(4-acetyl-3-hydroxy-2-propylphenoxy)methylbenzoic acid

A solution of 6.0 g (36.1 mmoles) of 3-methoxy-4-methylbenzoic acid in 120 ml of anhydrous MeOH was treated with 6 ml of acetyl chloride and stirred at room temperature for 36 hours. The MeOH was evaporated in vacuo followed by addition and evaporation of two 100 ml portion of methanol to give 6.34 g of methyl 3-methoxy-4-methylbenzoate colorless oil. This was carried through steps analogous to those in Example 1, steps b., c. and d.

The melting point of methyl 3-methoxy-4-(4-acetyl-3-hydroxy-2-propylphenoxy)methylbenzoate, was 128°–130° C. Recrystallization of the product of step d. from ethyl acetate gave 3-methoxy-4-(4-acetyl-3-hydroxy-2-propylphenoxy)methylbenzoic acid as a solid, mp 248°–250° C.

Analysis: Calculated for $C_{20}H_{22}O_6$: C, 67.03; H, 6.19. Found: C, 66.87; H, 6.32.

EXAMPLE 5

3-Nitro-4-(4-acetyl-3-hydroxy-2-propylphenoxy)methylbenzoic acid

Methyl 4-methyl-3-nitrobenzoate was prepared from 4-methyl-3-nitrobenzoic acid in the same manner as in Example 6. NMR in $CDCl_3$ ($\delta$units): 2.6 (singlet, 3); 3.9 (singlet, 3); 7.38 (doublet, 1); 8.1 (doublet, 1); and 8.53 (singlet, 1). This was carried through steps analogous to those in Example 1, steps b., c. and d.

Methyl 3-nitro-4-(4-acetyl-3-hydroxy-2-propylphenoxy)methylbenzoate was found to have a mp of 148.5°–150° C. The product of step d. was purified by chromatography using silica gel with a 5% by volume methanol in methylene chloride solution followed by evaporation of the solvents and washing of the residue with a 1:1 solution of methylene chloride:hexanes to yield 3-nitro-4-(4-acetyl-3-hydroxy-2-propylphenoxy)methylbenzoic acid as a solid, mp 226°–228° C.

Analysis: Calculated for $C_{19}H_{19}NO_7$: C, 61.12; H, 5.13. Found: C, 60.81; H, 5.41.

EXAMPLE 6

3-Fluoro-4-(4-acetyl-3-hydroxy-2-propylphenoxy)methylbenzoic acid

A solution of 10 g (0.065 mole) of 3-fluoro-4-methylbenzoic acid in 100 ml of anhydrous MeOH was treated with dry HCl gas and allowed to stand in a stoppered flask at room temperature for 60 hours. The MeOH was evaporated in vacuo and the dark oil obtained taken up in ether and dried with Na$_2$SO$_4$. The ether was evaporated in vacuo and the recovered oil filtered through a short column of silica gel with 50% CH$_2$Cl$_2$/hexane. Methyl 3-fluoro-4-methylbenzoate as a pale yellow oil (9.2 g) was recovered after removal of the solvents. This was then taken on through steps analogous to those in Example 1, steps b., c. and d.

Methyl 3-fluoro-4-(4-acetyl-3-hydroxy-2-propylphenoxy)methylbenzoate had a mp of 108°–110° C. The product was recrystallized to give 3-fluoro-4-(4-acetyl-3-hydroxy-2-propylphenoxy)methylbenzoic acid as a solid, mp 203°–206° C.

EXAMPLE 7

4-(4-Acetyl-3-hydroxy-2-propylphenoxy)methylphenoxyacetic acid a. Ethyl 4-bromomethylphenoxyacetate A solution of ethyl 4-methylphenoxyacetate, which may be prepared as set forth by S. G. Powell and R. Adams in J. Am. Chem. Soc., 42, pages 646–658 (1920), (18.21 g, 0.094 mole) in 100 ml of dry CCl$_4$ was stirred and refluxed under a 350 watt tungsten lamp. A solution of 15 g (0.094 mole) of bromine in 100 ml of CCl$_4$ was added by means of an addition funnel over a period of 30 minutes. The colorless reaction mixture was evaporated in vacuo and the resulting oil distilled bulb-to-bulb taking a middle cut at 120°–140° at 0.17 mm Hg.

b. Ethyl 4-(4-acetyl-3-hydroxy-2-propylphenoxy)methylphenoxyacetate

A solution of 1 g (5.15 mmoles) of 2,4-dihydroxy-3-propylacetophenone and 2.0 g (5.15 mmoles) of ethyl 4-bromomethylphenoxyacetate in 50 ml of dry acetone was stirred and refluxed with 800 mg of K$_2$CO$_3$ for 48 hours. The reaction mixture was diluted with H$_2$O, rendered acidic with 6N HCl and extracted into CH$_2$Cl$_2$. Evaporation of the CH$_2$Cl$_2$ gave an oil that was chromatographed on silica gel by gradient elution with 50% CH$_2$Cl$_2$/hexane to 75% CH$_2$Cl$_2$/hexane to provide the title compound as a white solid.

c. 4-(4-acetyl-3-hydroxy-2-propylphenoxy)methylphenoxyacetic acid

A solution of 180 mg (0.466 mmoles) of ethyl 4-(4-acetyl-3-hydroxy-2-propylphenoxy)methylphenoxy acetate in 10 ml of MeOH, 4 ml of tetrahydrofuran and 2 ml of water was treated with 40 mg (1.63 mmoles) of lithium hydroxide and stirred at room temperature for 6 hours. The reaction mixture was diluted with water, acidified by addition of 6 normal HCl and extracted with ether. The combined extracts were washed with water, dried (Na$_2$SO$_4$) and evaporated in vacuo to give 180 mg of solid. The solid was crystallized from CH$_2$Cl$_2$/hexane to give 100 mg of the title compound; mp 140°–142° C.

EXAMPLE 8

4-(4-Acetyl-3-hydroxy-6-iodo-2-propylphenoxy)methylbenzoic acid a. Methyl 4-(4-acetyl-3-hydroxy-6-iodo-2-propylphenoxy)methyl benzoate A solution of 308 mg (0.962 mmoles) of 2,4-dihydroxy-5-iodo-3-propyl acetophenone which may be obtained by the procedure of U.S. Pat. No. 4,252,818, and 497.2 mg (2.17 mmoles) of methyl 4-bromomethyl benzoate in 7 ml of 2-butanone was treated with 170.4 mg (1.23 mmoles) of K$_2$CO$_3$ and stirred at reflux for 21½ hours at which time 199.4 mg (1.20 mmoles) of KI were added and refluxed another 5 hours. The 2-butanone was removed by evaporation under reduced pressure and the residue was dissolved in ether, washed twice with water, once with saturated aqueous NaHCO$_3$ solution and dried with MgSO$_4$. Evaporation of solvent gave an oil which was chromatographed on silica gel eluting with 50% hexane/dichloromethane to provide 252 mg (55% yield) of a solid mp 70°–72° C.

b. 4-(4-Acetyl-3-hydroxy-6-iodo-2-propylphenoxy)methylbenzoic acid

A solution of 245 mg (0.523 mmoles) of methyl 4(-4-acetyl-3-hydroxy-6-iodo-2-propylphenoxy)methylbenzoate in 3 ml of tetrahydrofuran and 0.8 ml of water was treated with 110 mg (2.62 mmoles) of LiOH.H$_2$O and stirred at 22° C. for one hour. The temperature was brought to 55° C. and 3 ml of MeOH was added after 2 hours of reaction. After a total reaction time of 3½ hours, the mixture was allowed to cool, diluted with water, acidified by addition of concentrated HCl and extracted with dichloromethane. The combined extracts were washed with water, dried over MgSO$_4$ and evaporated to give 217 mg of white powder mp 167°–168.5° C.

Analysis: Calculated for C$_{19}$H$_{19}$O$_5$I: C, 50.23; H 4.22. Found: C, 50.63; H, 4.42.

EXAMPLE 9

3-[1-(4-Acetyl-3-hydroxy-2-propylphenoxy)ethyl]benzoic acid a. Methyl 3-acetylbenzoate A solution of 5 g of 3-acetylbenzoic acid in dry MeOH was saturated with hydrogen chloride gas. The reaction vessel was stoppered and kept at room temperature for 2 days. The MeOH was evaporated and the residue extracted into diethylether and clarified by filtration. The ether was evaporated and the dark oil was chromatographed through a short column of silica gel eluting with methylene chloride. The combined fractions were evaporated to dryness giving 4.25 g of a yellow oil that solidified on standing. The solid ester was used as obtained.

b. Methyl 3-(1-hydroxyethyl)benzoate

The crude ester from step a was dissolved in 50 ml of MeOH with 1.63 g of sodium cyanoborohydride and a trace of methyl orange. A solution of 2N methanolic hydrogen chloride was added dropwise at such a rate as to maintain a pH of 3 (stirring, red color). When the indicator remained permanent red, stirring was continued for 1.5 hours. The MeOH was evaporated and ether extraction provided the title compound. The crude product was carried forward without further purification.

c. Methyl 3-(1-bromoethyl)benzoate

The crude alcohol from step b was dissolved in 40 ml of dry toluene and cooled to 0°. The cold solution was stirred and treated dropwise with 6 g of phosphorous tribromide. Stirring was continued for 3.5 hours after which the reaction was poured onto ice and extracted with ether. Flash chromatography on silica gel, see W. C. Still et al. in the Journal of Organic Chemistry, Vol. 43, pages 2923–2925 (1978), eluting with hexanes, then 30% CH$_2$Cl$_2$/hexanes gave 2.78 g of a colorless oil.

d. Methyl 3-[1-(4-acetyl-3-hydroxy-2-propylphenoxy)ethyl]benzoate

In a manner analogous to that described in Example 1, step c., there was obtained 2.05 g of the title compound as a green-yellow oil. Flash chromatography on silica gel eluting with 30%–50% CH$_2$Cl$_2$/hexanes finally gave 1.6 g of the ester.

e. 3-[1-(4-Acetyl-3-hydroxy-2-propylphenoxy)ethyl]benzoic acid

The ester from step d. was saponified in the manner described in Example 1, step d. The crude material was crystallized from ether/hexanes which gave 0.58 g of analytically pure material, mp 101°–103° C.

Analysis: Calculated for C$_{20}$H$_{22}$O$_5$.¼H$_2$O: C, 69.24; H, 6.55. Found: C, 69.28; H, 6.44.

EXAMPLE 10

3-Ethoxy-4-(4-acetyl-3-hydroxy-2-propylphenoxy)methylbenzoic acid a. Methyl 3-ethoxy-4-methyl benzoate

A mixture of 3 g (18 mmoles) of methyl-3-hydroxy-4-methylbenzoate, 2.82 g (18.1 mmoles) ethyl iodide, 2.5 g (18.1 mmoles) potassium carbonate, and 60 ml dry acetone was refluxed 60 hours. The acetone was evaporated and the solid extracted with dilute aqueous HCl and ether. The ether layer was separated, washed with H$_2$O and dried with Na$_2$SO$_4$. Evaporation of the ether gave 2.8 g of white solid.

b. 3-Ethoxy-4-(4-acetyl-3-hydroxy-2-propylphenoxy)methylbenzoic acid

The material from step a was taken through steps analogous to those in Example 1, steps b., c., and d. Methyl 3-ethoxy-4-(4-acetyl-3-hydroxy-2-propylphenoxy)methylbenzoate by the step analogous to Example 1, step c. crystallized from hot ethyl acetate/hexanes, mp 152°–153° C. Recrystallization of the product from the step analogous to Example 1, step d. from MeOH/dilute aqueous hydrochloric acid gave 3-ethoxy-4-(4-acetyl-3-hydroxy-2-propylphenoxy)methylbenzoic acid, mp 226°–228° C.

Analysis: Calculated for C$_{21}$H$_{24}$O$_6$: C, 66.95; H, 6.57. Found: C, 66.83; H, 6.53.

EXAMPLE 11

2-Bromo-4-(4-acetyl-3-hydroxy-2-propylphenoxy)methylbenzoic acid

A solution of 10 g of 2-bromo-4-methylbenzoic acid in 100 ml of dry MeOH was saturated with hydrogen chloride gas. After 48 hours, the MeOH was evaporated and the amber oil so obtained was dissolved in ether and dried with Na$_2$SO$_4$. Evaporation of the ether gave material suitable for further transformation. This was carried through steps analogous to those in Example 1, steps b., c., and d. The methyl 2-bromo-4-(4-acetyl-3-hydroxy-2-propylphenoxy)methylbenzoate intermediate was purified by flash column chromatography on silica gel eluting with 25% CH$_2$Cl$_2$/hexanes up to 100% CH$_2$Cl$_2$ and was obtained as a white solid, mp 80°–83°. The product of the step analogous to Example 1, step d. was crystallized from ethanol/water and gave 2-bromo-4-(4-acetyl-3-hydroxy-2-propyl-phenoxy)methylbenzoic acid as a white fluffy solid, mp 181°–183° C.

Analysis: Calculated for C$_{19}$H$_{19}$BrO$_5$: C, 55.40; H, 4.78. Found: C, 55.49; H, 4.67.

EXAMPLE 12

2-Methoxy-4-(4-acetyl-3-hydroxy-2-propylphenoxy)methylbenzoic acid

Methyl 2-hydroxy-4-methylbenzoate was prepared from the acid by the method described in Example 6. It was then converted to methyl 2-methoxy-4-methylbenzoate in a manner analogous to that described in Example 10, step a. to provide a pale yellow oil. This material was then carried through steps analogous to those in Example 1, steps b., c., and d. The title compound was obtained as an analytically pure white solid from MeOH/H$_2$O, mp 143°–145° C.

Analysis: Calculated for C$_{20}$H$_{22}$O$_6$: C, 67.02; H, 6.19. Found: C, 66.70; H, 6.24.

EXAMPLE 13

4-[1-(4-Acetyl-3-hydroxy-2-propylphenoxy)benzyl]benzoic acid

4-Carbomethoxybenzophenone was prepared by the method described in Example 6 from 4-benzoylbenzoic acid. It was then converted to 4-carbomethoxydiphenyl bromomethane in an analogous way as described in Example 9, steps b. and c. to give a colorless oil, bp 165° C. at 0.35 mm of Hg. This compound was then transformed by steps analogous to those in steps d. and e. of Example 9. The product of step d. was obtained as pale pink crystals, mp 133°–135° C., from hot ethanol. The title compound from step e. was crystallized from hot ethanol/hexanes, mp 134°–136° C.

Analysis: Calculated for C$_{25}$H$_{24}$O$_5$.¼H$_2$O: C, 73.4; H, 6.05. Found: C, 73.4; H, 6.23.

EXAMPLE 14

4-[3-(4-Acetyl-3-hydroxy-2-propylphenoxy)]propen-1-yl benzoic acid a. 4-Carbomethoxycinnamaldehyde

A solution of 0.21 g (1.25 mmoles) of 4-carbomethoxybenzaldehyde, 0.42 g (1.25 mmoles) of formylmethylenetriphenylphosphorane and a catalytic amount of benzoic acid in 25 ml of THF was refluxed under nitrogen for 18 hours. The THF was evaporated and the recovered gum extracted repeatedly with ether. The combined ether extracts were evaporated. Flash chromatography on silica gel with 50% CH$_2$Cl$_2$/hexane up to 100% CH$_2$Cl$_2$ gave 90 mg of a white solid.

b. 4-Carbomethoxycinnamyl alcohol

A solution 100 mg (0.89 mmoles) of the aldehyde from step a. in methanol was treated with 33.65 mg (0.89 mmoles) of NaBH$_4$ in one portion. The reaction was over in 20 minutes, when TLC (silica gel, CH$_2$Cl$_2$) indicated lack of aldehyde in the reaction mixture. The reaction was diluted with H$_2$O, acidified with 6M HCl and extracted with ether. The ether extracts were combined, washed with H$_2$O and dried with Na$_2$SO$_4$. Evaporation of the ether gave crude alcohol that was carried on to step c.

c. 4-Carbomethoxycinnamyl bromide

Crude cinnamyl alcohol from step b. was treated with excess PBr₃ in toluene at room temperature.

The reaction was allowed to proceed overnight in a stoppered flask followed by pouring onto ice. Ether extraction provided a solid which was crystallized from hexane to give 100 mg of the product.

d. 4-[3-(4-Acetyl-3-hydroxy-2-propylphenoxy)propen-1-yl]benzoic acid

The title compound was prepared by methods analogous to those described in Example 1, steps c. and d. The methyl ester intermediate was purified by flash chromatography on silica gel ($CH_2Cl_2$) and isolated as pale yellow crystals. NMR (250 MHz, $CDCl_3$) supported the structure assignment. Crystallization from $MeOH/H_2O$ with cooling gave the title compound, mp 195°–198° C.

Analysis: Calculated for $C_{21}H_{22}O_5$: C, 71.17; H, 6.26. Found: C, 71.13; H, 6.49.

EXAMPLE 15

2-Bromo-5-methoxy-4-(4-acetyl-3-hydroxy-2-propylphenoxy)methylbenzoic acid a. Methyl 3-hydroxy-4-methylbenzoate

The ester was prepared by a method analogous to that described in Example 6.

b. Methyl 2-bromo-5-hydroxy-4-methylbenzoate

A solution of 1 g (6 mmoles) of the ester from step a. dissolved in 10 ml of dry $CH_2Cl_2$ and cooled in an ice bath was treated dropwise with 0.96 g (6 mmoles) of $Br_2$ in 2 ml $CH_2Cl_2$. The reaction flask was sealed and stored at −15° overnight. Gentle swirling of the reaction solution induced crystallization of fine white needles that were collected by filtration and washed with cold $CH_2Cl_2$/hexanes.

c. Methyl 2-bromo-5-methoxy-4-methylbenzoate

A mixture of 800 mg of material from step b. 10 ml of dry reagent grade acetone, 456 mg of $K_2CO_3$, and excess methyl iodide was stirred a refluxed for 3 days. Ether extraction provided the ester in a form suitable for further transformation.

d. 2-Bromo-5-methoxy-4-(4-acetyl-3-hydroxy-2-propylphenoxy)methylbenzoic acid The title compound was prepared by methods analogous to those described in Example 1, steps b., c., and d. The ester intermediate product from the step analogous to Example 1, step c. had an mp of 192°–193°. The title compound precipitated from the reaction mixture upon acidification with 6M HCl (pH less than 3) and was obtained analytically pure, after washing with hot MeOH and drying, mp 237°–238° C.

Analysis: Calculated for $C_{20}H_{21}BrO_6 \cdot \frac{1}{4} H_2O$: C, 54.36; H, 4.91. Found: C, 54.22; H, 4.94.

EXAMPLE 16

4-(4-Acetyl-3-hydroxy-2-propylphenoxy)methylcinnamic acid a. Methyl 4-methylcinnamate

A solution of 6.0 g (37.0 mmol) of 4-methylcinnamic acid in 120 ml of anhydrous MeOH was treated with 6 ml of acetyl chloride and stirred at reflux for 18 hours. Evaporation of the MeOH gave the title ester as a white solid, mp 53.5°–57.5° C.

b. Methyl 4-bromomethylcinnamate

A mixture of 3.0 g (17.03 mmol) of methyl 4-methylcinnamate, 3.33 g (18.73 mmol) of N-bromosuccinimide and 60 mg of 2,2′-azobis(2-methylpropionitrile) in 75 ml of carbon tetrachloride was heated to reflux with a heat lamp and stirred rapidly for 30 minutes. The reaction mixture was cooled to room temperature and filtered. The filtrate was evaporated to give the title compound as an oil which crystallized. NMR in $CDCl_3$ ($\delta$ units): 3.80 (singlet, 3); 4.48 (singlet, 2); 6.44 and 7.67 (doublets, J=15 Hz, 1); 7.39, 7.49 (doublets, J=7 Hz, 2).

c. Methyl 4-(4-acetyl-3-hydroxy-2-propylphenoxy)methylcinnamate

A mixture of 1.0 g (5.15 g) of 2,4-dihydroxy-3-propylacetophenone, 1.58 g (6.18 mmol) of methyl 4-bromomethylcinnamate and 0.85 g (6.18 mmol) of anhydrous potassium carbonate in 20 ml of acetone was stirred at reflux for 18 hours. Ether extraction gave 1.01 g of the title compound as a light yellow powder mp 121°–125° C.

d. 4-(4-Acetyl-3-hydroxy-2-propylphenoxy)methylcinnamic acid

A solution of 1.0 g (2.71 mmol) of methyl 4-(4-acetyl-3-hydroxy-2-propylphenoxy)methylcinnamate and 569 mg (13.57 mmol) of lithium hydroxide, monohydrate, in a mixture of 9 ml of MeOH, 9 ml of THF and 2 ml of water was stirred at 50° C. for 2 hours. The reaction mixture was cooled to room temperature, diluted with 100 ml of 0.5N HCl solution to give a fine white precipitate. The precipitate was isolated by filtration and recrystallized from ethanol to give 750 mg of the title compound as a fine, white cottony solid; mp 203°–204° C.

Analysis: Calculated for $C_{21}H_{22}O_5$: C, 71.17; H, 6.26. Found: C, 71.07; H, 6.39.

EXAMPLE 17

3-(4-Acetyl-3-hydroxy-2-propylphenoxy)methylphenylacetic acid

Methyl 3-methylphenylacetate was prepared from 3-methylphenylacetic acid in the same manner as in Example 4. This was carried through steps analogous to those in Example 1, steps b., c., and d.

Methyl 3-(4-acetyl-3-hydroxy-2-propylphenoxy)methylphenylacetate was found to have an mp of 78°–79° C. The product from the analogous step d. was recrystallized from ethanol-water to give the pure title compound, mp 156.5°–157.5° C.

Analysis: Calculated for $C_{20}H_{22}O_5$: C, 70.16; H, 6.48. Found: C, 70.18; H, 6.44.

EXAMPLE 18

2-Methoxy-5-(4-acetyl-3-hydroxy-2-propylphenoxy)methylcinnamic acid a. Methyl cis-2-methoxy-5-methylcinnamate

A stirred solution of 6.0 g (37.46 mmol) of 6-methylcoumarin in 100 ml of dimethylformamide was treated with 3.29 g (82.41 mmol) of sodium hydroxide in 10 ml of water. After 15 minutes, 26.6 g (187.3 mmol) of methyl iodide was added. After an additional 6 hours, ether extraction provided the title compound as an oil. NMR in CDCl$_3$ ($\delta$ units): 2.28 (singlet, 3); 3.66 (singlet, 3); 3.79 (singlet, 3); 5.97 and 7.13 (doublet, J=12 Hz, 1); 6.76 (doublet, J=8 Hz, 1); 7.09 (broad doublet, 1); 7.35 (broad singlet, 1).

b. Methyl trans-2-methoxy-5-bromomethylcinnamate

As described in step b. of Example 16 methyl cis-2-methoxy-5-methylcinnamate was treated with N-bromosuccinimide in carbon tetrachloride to provide the oily title compound which was purified by chromatography on silica gel with ether/hexane: NMR in CDCl$_3$ ($\delta$ units) 3.76 and 3.83 (singlet, 3); 4.43 (singlet, 2); 6.47 and 7.92 (doublet, J=16 Hz, 1); 6.83 (doublet, J=9 Hz, 1); 7.65 (multiplet, 2).

c. 2-Methoxy-5-(4-acetyl-3-hydroxy-2-propylphenoxy)-methylcinnamic acid

Methyl 2-methoxy-5-bromomethylcinnamate was carried through steps analogous to these in Example 16, steps c. and d.

Methyl 2-methoxy-5-(4-acetyl-3-hydroxy-2-propylphenoxy)methylcinnamate melted at 127°–129° C. 2-Methoxy-5-(4-acetyl-3-hydroxy-2-propylphenoxy)-methylcinnamic acid was recrystallized from ethanol to give yellow plates: mp 196.5°–198° C.

Analysis: Calculated for $C_{22}H_{24}O_6$: C, 68.74; H, 6.29. Found: C, 68.38; H, 6.35.

EXAMPLE 19

2-Methoxy-4-(4-acetyl-3-hydroxy-2-propylphenoxy)-methylcinnamic acid

The title compound was prepared by methods analogous to those in Example 18, steps a., b. and c. Recrystallization of the title compound from ethanol gave a light yellow powder, mp 214°–216° C.

Analysis: Calculated for $C_{22}H_{24}O_6$: C, 68.74; H, 6.29. Found: C, 68.59; H, 6.27.

EXAMPLE 20

3-(4-Acetyl-3-hydroxy-2-propylphenoxy)methylcinnamic acid a. Methyl 3-methylcinnamate A mixture of 6.0 g (49.9 mmol) of m-tolualdehyde and 18.37 g (54.93 mmol) of methyl (triphenylphosphoranylidene)acetate in 50 ml of THF was stirred at reflux for 4 hours. The THF was evaporated and the residue was stirred with 200 ml of petroleum ether (bp=30°–60° C.) and filtered. The filtrate was evaporated to give the title compound as a light yellow liquid which was distilled bulb-to-bulb at 90° C./0.4 mm of Hg.

b. 3-(4-Acetyl-3-hydroxy-2-propylphenoxy)methylcinnamic acid

Methyl 3-methylcinnamate was carried through steps analogous to those in Example 16, steps b., c. and d. Methyl 3-(4-acetyl-3-hydroxy-2-propylphenoxymethyl-cinnamate had an mp of 113°–115° C. The title compound was recrystallized from ethanol to give white flocculent crystals, mp 195°–196° C.

Analysis: Calculated for $C_{21}H_{22}O_5$: C, 71.17; H, 6.26. Found: C, 71.07; H, 5.98.

EXAMPLE 21

4-Methoxy-3-(4-acetyl-3-hydroxy-2-propylphenoxy)-methylcinnamic acid a. Methyl 3-methyl-4-methoxycinnamate Treatment of 3-methyl-4-methoxybenzaldehyde with methyl(triphenylphosphoranylidene)acetate in a procedure analogous to that described in Example 20, step a. provided methyl 3-methyl-4-methoxycinnamate which was recrystallized from hexane to give white crystals, mp 70°–73° C.

b. 4-Methoxy-3-(4-acetyl-3-hydroxy-2-propylphenoxy)-methylcinnamic acid

Methyl 3-methyl-4-methoxycinnamate was carried through steps analogous to those described in Example 16, steps b., c. and d. Methyl 4-methoxy-3-(4-acetyl-3-hydroxy-2-propylphenoxy)methylcinnamate melted at 141°–143° C. The title compound was recrystallized from ethanol to give flocculent needles, mp 245°–246° C.

Analysis: Calculated for $C_{22}H_{24}O_6$: C, 68.74; H, 6.29. Found: C, 68.72; H, 6.34.

EXAMPLE 22

3-Methoxy-4-(4-acetyl-3-hydroxy-2-propylphenoxy)-methylcinnamic acid a. 3-Methoxy-4-methylbenzoyl chloride A mixture of 10.0 g (60.17 mmol) of 3-methoxy-4-methylbenzoic acid, 15 ml (210 mmol) of thionyl chloride and 10 ml of toluene was stirred at reflux for 2 hours. The solvents were then evaporated and the residue was distilled bulb-to-bulb at 60°–70° C. at a pressure of 0.04 mm of Hg to give the title compound as a colorless liquid.

b. 3-Methoxy-4-methylbenzaldehyde

A mixture of 5.0 g (27.08 mmol) of 3-methoxy-4-methylbenzoyl chloride, 4.0 ml (34.34 mmol) of 2,6-lutidine and 400 mg of 10% palladium on carbon in 40 ml of THF was rapidly stirred under an atmosphere of hydrogen until no more hydrogen was taken up. Filtration and extraction with ethyl acetate gave title compound as a light yellow oil.

c. 3-Methoxy-4-(4-acetyl-3-hydroxy-2-propylphenoxy)-methylcinnamic acid

Conversion of 3-methoxy-4-methylbenzaldehyde to methyl 3-methoxy-4-methylcinnamate was carried out by a procedure analogous to that described in Example 20, step a. This product was then carried on to the title compound by procedures similar to those described in Example 16, steps b., c. and d. Methyl 3-methoxy-4-(4-acetyl-3-hydroxy-2-propylphenoxy)methylcinnamate was recrystallized from ethanol to give a light yellow powder, mp 144°–146° C. The title compound was recrystallized from ethanol to give light yellow, fine needles, mp 203°–204.5° C.

Analysis: Calculated for $C_{22}H_{24}O_6$: C, 68.74; H, 6.29. Found: C, 68.55; H, 6.43.

EXAMPLE 23

4-β-(4-Acetyl-3-hydroxy-2-propylphenoxy)ethyl benzoic acid

A mixture of 1 g (5.55 mmoles) of 2,4-dihydroxy-3-propylacetophenone, 1.27 g (5.55 mmoles) of para-(β-bromoethyl)benzoic acid, 2.4 g of potassium carbonate, and 50 ml of dry acetone was stirred and refluxed for 3 days. The reaction flask was cooled and the stirred mixture was diluted with $H_2O$ and acidified with 6N HCl. Extraction with ethyl acetate and drying with $Na_2SO_4$ afforded the crude product after evaporating the ethyl acetate in vacuo. Pure 4-β-(4-acetyl-3-hydroxy-2-propylphenoxy)ethyl benzoic acid was isolated by flash chromatography on silica gel eluting with 5% $MeOH/CH_2Cl_2$ containing 0.1% acetic acid.

What is claimed is:

1. A compound of the following formula (I); (II) or (III):

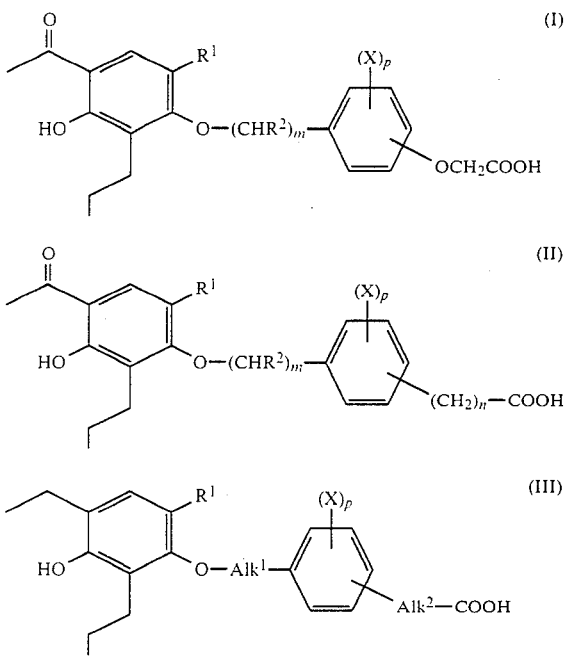

wherein
$R^1$ is hydrogen or iodine;
$R^2$ is hydrogen, lower alkyl, phenyl or phenyl substituted with one to three halogen, alkyl or alkoxy groups;
X is independently halogen, nitro, hydroxy, lower alkyl or lower alkoxy;
$Alk^1$ is methylene;
$Alk^2$ is alkenyl of 2 or 3 carbon atoms;
m is 1;
n is 0 or 1; and
p is 0, 1 or 2
or a pharmaceutically acceptable base-addition salt thereof.

2. A compound of claim 1, said compound being of the formula (I) wherein
$R^1$ is hydrogen; $R^2$ is hydrogen; p is 0; and the —$OCH_2COOH$ group is meta or para.

3. A compound of claim 1, said compound being of the formula (II) wherein $R^1$ is hydrogen; $R^2$ is hydrogen; n is 0; and the —COOH group is para to the —$CHR^2$— group;
$R^1$ is hydrogen; $R^2$ is methyl or phenyl; p is 0; n is 0; and the —COOH group is para to the —$CHR^2$— group;
$R^1$ is hydrogen; $R^2$ is hydrogen; p is 0; n is 1; and the —$CH_2COOH$ group is meta or para to the —$CHR^2$— group;
$R^1$ is hydrogen; $R^2$ is hydrogen; n is 0; p is 1; X is lower alkoxy and is ortho to the —$CHR^2$— group; and the —COOH group is para to the —$CHR^2$— group; or
$R^1$ is hydrogen; $R^2$ is hydrogen; n is 0; p is 1; X is halogen and is meta to the —$CHR^2$— group; and the —COOH group is para to the —$CHR^2$— group.

4. A compound of claim 1, said compound being of the formula (III) wherein
$R^1$ is hydrogen; $Alk^1$ is methylene; p is 0; $Alk^2$ is trans ethenyl and is meta or para to $Alk^1$; or
$R^1$ is hydrogen; $Alk^1$ is methylene; p is 1; X is lower alkoxy and is ortho to $Alk^1$; $Alk^2$ is trans ethenyl and is meta or para to $Alk^1$.

5. A compound of claim 1, wherein
$R^1$ is hydrogen;
$R^2$ is hydrogen, lower alkyl or phenyl;
X is fluoro, chloro, bromo, iodo, methyl, ethyl, propyl, butyl, methoxy, propoxy or butoxy;
$Alk^1$ is methylene;
$Alk^2$ is alkenyl of 2 or 3 carbon atoms;
m is 1;
n is 0 or 1; and
p is 0 or 1.

6. A pharmaceutical composition comprising a compound of claim 1 and a pharmaceutically acceptable carrier or diluent.

7. A method of antagonizing the slow reacting substance of anaphylaxis or components thereof in a warm blooded animal comprising administering to the animal the pharmaceutical composition of claim 6.

8. A method of preparing a compound of claim 1 comprising saponifying a corresponding ester.

9. A compound of claim 1, which is
4-(4-acetyl-3-hydroxy-2-propylphenoxy)methylphenoxyacetic acid;
3-methoxy-4-(4-acetyl-3-hydroxy-2-propylphenoxy)-methylbenzoic acid;
4-(4-acetyl-3-hydroxy-2-propylphenoxy)methylcinnamic acid; or
3-methoxy-4-(4-acetyl-3-hydroxy-2-propylphenoxy)-methylcinnamic acid,
or a pharmaceutically-acceptable base-addition salt thereof.

10. A compound of the following formula (VI) or (VIII):

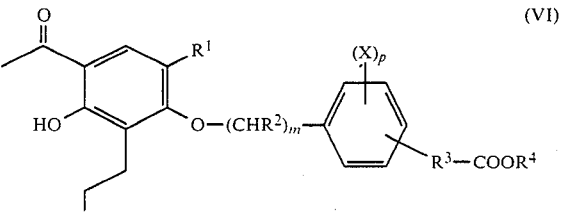

-continued

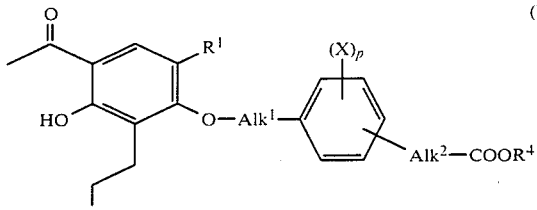
(VIII)

wherein
$R^1$ is hydrogen or iodine;
$R^2$ is hydrogen, lower alkyl, phenyl or phenyl substituted with one to three halogen, alkyl or alkoxy groups;
X is independently halogen, nitro, hydroxy, lower alkyl or lower alkoxy;
$Alk^1$ is methylene;
$Alk^2$ is alkenyl of 2 or 3 carbon atoms;
$R^3$ is —O—$CH_2$— or —$(CH_2)_n$—;
m is 1;
n is 0 or 1;
p is 0, 1 or 2; and
$R^4$ is an organic moiety which is replaceable by hydrogen.

11. A compound of claim 10, wherein said compound is of the formula (VI).

12. A compound of claim 10, wherein said compound is of the formula (VIII).

13. A compound of claim 10 in which $R^4$ is lower alkyl.

14. A compound selected from the group consisting of:
4-(4-acetyl-3-hydroxy-2-propylphenoxy)methylbenzoic acid;
2-(4-acetyl-3-hydroxy-2-propylphenoxy)methylbenzoic acid;
3-(4-acetyl-3-hydroxy-2-propylphenoxy)methylbenzoic acid;
3-methoxy-4-(4-acetyl-3-hydroxy-2-propylphenoxy)-methylbenzoic acid;
3-nitro-4-(4-acetyl-3-hydroxy-2-propylphenoxy)methylbenzoic acid;
3-fluoro-4-(4-acetyl-3-hydroxy-2-propylphenoxy)methylbenzoic acid;
4-(4-acetyl-3-hydroxy-2-propylphenoxy)methylphenoxyacetic acid;
4-(4-acetyl-3-hydroxy-6-iodo-2-propylphenoxy)methylbenzoic acid;
3-[1-(4-acetyl-3-hydroxy-2-propylphenoxy)ethyl]benzoic acid;
3-ethoxy-4-(4-acetyl-3-hydroxy-2-propylphenoxy)methylbenzoic acid;
2-bromo-4-(4-acetyl-3-hydroxy-2-propylphenoxy)methylbenzoic acid;
2-methoxy-4-(4-acetyl-3-hydroxy-2-propylphenoxy)-methylbenzoic acid;
4-[1-(4-acetyl-3-hydroxy-2-propylphenoxy)benzyl]benzoic acid;
2-bromo-5-methoxy-4-(4-acetyl-3-hydroxy-2-propylphenoxy)methylbenzoic acid;
4-(4-acetyl-3-hydroxy-2-propylphenoxy)methylcinnamic acid;
3-(4-acetyl-3-hydroxy-2-propylphenoxy)methylphenylacetic acid;
2-methoxy-5-(4-acetyl-3-hydroxy-2-propylphenoxy)-methylcinnamic acid;
2-methoxy-4-(4-acetyl-3-hydroxy-2-propylphenoxy)-methylcinnamic acid;
3-(4-acetyl-3-hydroxy-2-propylphenoxy)methylcinnamic acid;
4-methoxy-3-(4-acetyl-3-hydroxy-2-propylphenoxy)-methylcinnamic acid; and
3-methoxy-4-(4-acetyl-3-hydroxy-2-propylphenoxy)-methylcinnamic acid;
and the pharmaceutically-acceptable base-addition salts thereof.

* * * * *